| United States Patent [19] | [11] Patent Number: 4,950,610 |
| --- | --- |
| Tittle | [45] Date of Patent: Aug. 21, 1990 |

[54] TITRATING APPARATUS AND METHOD

[75] Inventor: Douglas L. Tittle, Willoughby, Ohio

[73] Assignee: Man-Gill Chemical Company, Cleveland, Ohio

[21] Appl. No.: 101,387

[22] Filed: Sep. 28, 1987

[51] Int. Cl.$^5$ .............................................. G01N 31/16
[52] U.S. Cl. ...................................... 436/163; 436/51; 422/75; 422/76; 422/77; 356/229; 356/435
[58] Field of Search ................................... 422/75–77; 436/51, 163; 356/435, 229

[56] References Cited

U.S. PATENT DOCUMENTS

| | | | |
| --- | --- | --- | --- |
| 2,726,936 | 12/1955 | Bernheim | 422/77 |
| 2,960,910 | 11/1960 | Pelavin | 88/14 |
| 3,031,917 | 5/1962 | Pelavin | 88/14 |
| 3,236,148 | 2/1966 | Pelavin | 88/14 |
| 3,422,271 | 1/1969 | Fuhrmann | 250/218 |
| 3,707,455 | 12/1972 | Derr et al. | 204/195 P |
| 4,033,330 | 7/1977 | Willis et al. | 128/2 |
| 4,537,510 | 8/1985 | Takahasi | 356/435 |
| 4,613,947 | 9/1986 | Suzuku et al. | 364/526 |
| 4,749,552 | 6/1988 | Sakisako et al. | 422/75 |

FOREIGN PATENT DOCUMENTS 0720399  3/1980  U.S.S.R. ............................... 422/75

OTHER PUBLICATIONS

Theburn et al., "Development of a Commercial Automatic Colorimetric titrator", Anal. Chem., pp. 124–128, Jan. 1959.

*Primary Examiner*—Barry S. Richman
*Assistant Examiner*—Lynn M. Kummert
*Attorney, Agent, or Firm*—Renner, Otto, Boisselle & Sklar

[57] ABSTRACT

Titration apparatus includes two cells that receive and contain liquids and are transparent to light. A liquid having an unknown characteristic and mixed with an indicator that is optically responsive to a titrant is disposed in the cells. Light is transmitted through each cell to separate photosensors. The photosensor signals are compared and a titrant is added to one of the cells in known-volume increments until the difference between the signals reaches or exceeds a prescribed threshold. The characteristic of the liquid is calculated from the quality of known concentration titrant added in order to reach or exceed the prescribed threshold.

24 Claims, 1 Drawing Sheet

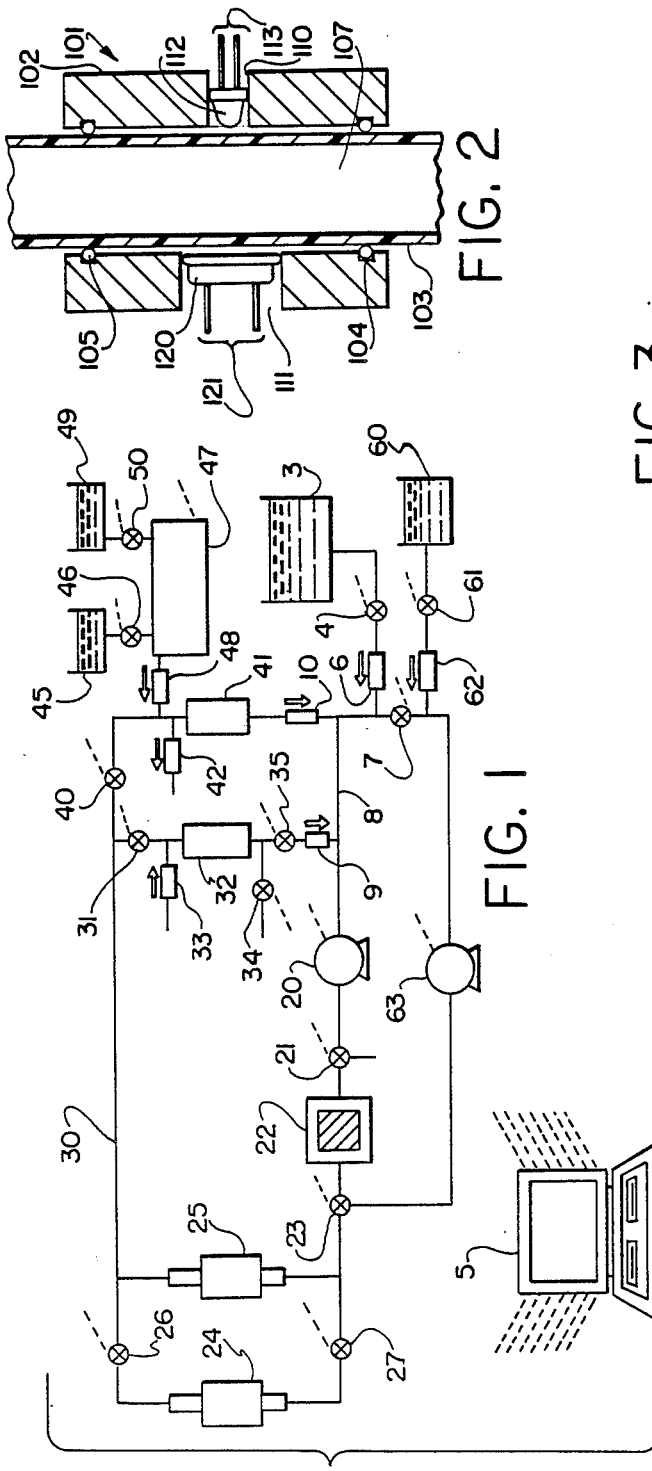
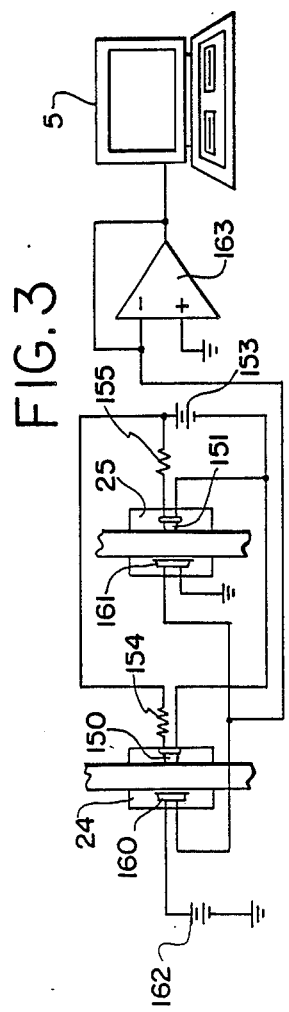
FIG. 1
FIG. 2
FIG. 3

TITRATING APPARATUS AND METHOD

BACKGROUND

Titration is a well known method for determinating a concentration of a constituent of a solution or for determining a characteristic of a solution. In traditional titration acidity or alkalinity is determined by adding an acid or base to a solution containing an indicator. When the pH reaches a particular value, the color of the indicator changes. For example, a common indicator is phenolpthalein which is colorless in acidic solutions, but is red in solutions having a pH exceeding nine. Other well known indicators that change colors at particular pH's are: methyl orange xylene cyanol, methyl red, litmus, and bromophenol blue. Other indicators are available for responding to the presence of particular ions in solution. For example, permanganate ions respond to the presence of iron or nitrite ions in solution. A characteristic of a solution containing an indicator may be determined from the quantity of a titrant of known concentration (e.g., acidity) added to the solution to bring about a change in indicator color.

Titrations are conveniently carried out in a laboratory environment with relatively inexpensive apparatus since conditions can be easily controlled. However, in manufacturing operations where conditions are not so easily controlled, employment of titration to test or analyze and thereby control the characteristics of various chemical baths is more difficult and expensive. In many situations, analytical techniques other than titration are employed to monitor characteristics of solutions, such as plating baths, including spectroscopy techniques that require expensive and complex apparatus.

In manufacturing operations, titration can be an effective means of determining when a chemical bath requires replenishment or addition of make-up chemicals to maintain characteristics within a desired range. Yet, employment of titration as a process control technique has been retarded because available apparatus is complex making it difficult to maintain and expensive to purchase and install. Accordingly, there is a need for an automated, inexpensive titration apparatus for use in process control.

SUMMARY OF THE INVENTION

In the invention, two cells, that are transparent to light and can contain a liquid, are connected to receive a liquid having a chemical characteristic that is to be determined. The cells are hydraulically connected in parallel and actuatable valves permit the first of the cells to be isolated from a hydraulic circuit. The circuit includes a pump for circulating a liquid through the cell and may include a filter for removing particulate matter from liquids circulating through one or both of the cells. A sample liquid is drawn into the apparatus and circulated through a hydraulic circuit. During the circulation, an indiator is added to the liquid, preferably in a known quantity. The indicator alters the optical characteristics of the liquid and is optically responsive to a particular reagent, the titrant.

One or more sources of light are disposed to transmit a beam of light through the cells. Separate photosensors are disposed on opposite sides of the cells for detecting the relative amount of light passing through the cells. The photosensors produce electrical signals indicative of the amount of light transmitted through the cells to the sensors.

After sufficient mixing of the indicator and liquid, the first cell is isolated from the hydraulic circuit. Thereafter, a known-concentration titrant is added, at intervals, to the mixed liquid and indicator circulating through the second cell. The relative amounts of light transmitted through the first and second cells are compared by comparing the electrical signals produced by their respective photosensors. After an initial comparison, additional titrant is added, preferably in known-volume increments, until the difference between the signals produced by the photosensors reaches or exceeds a prescribed, threshold value. The threshold difference value corresponds to a substantial change in optical characteristics brought about by the interaction of the titrant and indicator.

The quantity of titrant added to produce the threshold optical change is preferably determined by counting the number of known-volume increments of titrant added. Preferably, the titrant is added by an electrically driven pump responding to electrical pulses so that the added volume can be determined by counting the number of pulses applied to the pump. Alternatively, the volume of titrant added by a peristaltic pump can be determined from the known pumping rate multiplied by the duration of the pump's operation.

Since the concentration of the titrant is known, from the titration process a characteristic of the liquid, such as free acidity, total acidity, a particular ion concentration, or the like, can be calculated. Preferably, the apparatus and the process and controlled by a computer. The computer controls periodic sampling of the liquid, addition of indicator and titrant, calculates the characteristic of the liquid that is of interest and flushes the apparatus in preparation for a subsequent titration. The computer controls valves employed in the hydraulic circuit to carry out the process steps. Preferably, the computer also includes a reference routine to establish the threshold value and as a self-test to indicate whether the apparatus is functioning normally.

BRIEF DESCRIPTION OF THE DRAWINGS

In the annexed drawings:

FIG. 1 is a schematic diagram of the hydraulic arrangement of añ apparatus according to an embodiment of the invention;

FIG. 2 is a sectional side view of a test cell embodiment for use in the invention; and FIG. 3 is a schematic diagram of an embodiment of electrical circuitry for use in the invention.

DETAILED DESCRIPTION OF PREFERRED EMBODIMENTS

In FIG. 1 a diagram of the hydraulic interconnections of a preferred embodiment of an apparatus according to the invention is shown schematically. The apparatus is employed to analyze and/or control liquid mixtures or solutions and is particularly useful in continuous manufacturing operations, such as electroplating, phosphating and other metal treatments. Vessel 3 represents a vat or other container holding a liquid mixture or solution that is to be monitored and/or controlled to maintain a particular characteristic. For example, it may be desirable to monitor the acidity, alkalinity or iron or nitrite content of the liquid in vessel 3 to maintain that characteristic within established quality control limits. When those limits are approached or exceeded, a warning may be issued to take action or reagents may be automatically added to vessel 3 to maintain the desired characteristic within the desired range.

In order to determine the characteristic of the liquid, some of the liquid is drawn from vessel 3 and supplied to the novel titration apparatus. Piping or tubing leads from vessel 3 to an actuable valve 4. Valve 4 may be a conventional solenoid, pneumatic or hydraulic valve, as are all of the other valves in FIG. 1 except for those differently indentified. Preferably the valves are electrically actuable. The angular dashed lines extending from the valves, such as valve 4, indicate an electrical connection to an electrical control apparatus, such as a computer 5. For clarity, the complete connection between electrically operated components in FIG. 1 and computer 5 are not drawn but are indicated by the broken lines extending from the electrically controlled elements and from computer 5. While it is preferred to control the apparatus of FIG. 1 with a computer because of its flexibility, simpler control means, such as a programmed, electrically driven drum, or the like, may be substituted for the computer.

Liquid flowing from vessel 3 through valve 4, when that valve is open, passes through a check valve 6 and into a hydraulic circuit of FIG. 1. Check valve 6 prevents liquid that may be present elsewhere in the tubing from flowing back into vessel 3. During the process of abstracting liquid from vessel 3 for determination of a chemical characteristic, an electrically operated valve 7 is normally closed. Therefore the sampled liquid flows from vessel 3 into tubing 8.

Tubing 8 comprises a portion of a hydraulic circuit that includes four legs hydraulically connected in parallel. The legs on the right side of the diagram include check valves 9 and 10, respectively, that prevents fluid flowing into the circuit from directly entering those legs. The liquid thus proceeds along tubing 8 to an electrically driven pump 20 for circulating liquid within the hydraulic loop and through any legs of the circuit that are open for fluid flows.

Fluid pumped out of pump 20 passes through a normally open, remotely operated valve 21, thereafter through a filter 22 and finally through a second normally open, remotely operated valve 23. Filter 22 and valves 21 and 23 are optional elements of the hydraulic loop. Filter 22 is important if the liquid being monitored is likely to contain particulate matter. As explained below, the process for determining a characteristic of the liquid requires the transmission of light through a liquid sample. The presence of particulate matter can cause light scattering that can interfere with the light transmission. Filter 22 removes the potentially interfering particulate matter. Unlike the other electrically operated valves present in the hydraulic circuit, valves 21 and 23 are not merely opened and closed, but when actuated provide alternative liquid flow paths. As explained below in connection with the discussion concerning cleaning the hydraulic circuit, valves 21 and 23 permit a reverse liquid flow through filter 22 in order to clean the filter.

Liquid being monitored that passes through valve 23 when that valve is open, i.e. the normal situation, may enter either or both the two leftmost parallel legs of the hydraulic circuitry. Those legs contain test cells 24 and 25, respectively. The tests cells are intended to receive and retain a liquid sample for transmission of light through the sample. A detailed description of the structure of an embodiment of a test cell is provided below in connection with FIG. 2. The parallel leg of the hydraulic circuit containing cell 24 may be hydraulically isolated by closing remotely actuated valves 26 and 27 disposed on opposite sides of cell 24.

Liquid flowing from cell 25 and, if not isolated, cell 24 by virtue of the circulation driven by pump 20, is transmitted through tubing 30 to the rightmost parallel legs of the hydraulic circuit. Each of these legs can be hydraulically isolated by remotely actuated valves. In the first of the legs to be encountered by flowing liquid, a remotely actuated valve 31 controls whether the leg is open to flowing liquid. Liquid passing through valve 31 reaches a reservoir 32. Reservoir 32 provides additional volume needed to draw a sufficient quantity of liquid into the hydraulic loop to fill the loop at the beginning of the sampling cycle. In order that reservoir 32 can be drained when desired, a check valve 33, for admitting air into reservoir 32, is hydraulically connected to the input tubing to reservoir 32. The outlet of reservoir 32 is connected to two remotely actuated valves 34 and 35. Valve 34 is normally closed, but may be opened to drain any liquid from reservoir 32. The outlet tubing from valve 34 is directed to a drain or sump not shown in FIG. 1. Valve 35 connects the outlet tubing from reservoir 32 to the hydraulic loop in tubing 8 through check valve 9. Normally, valves 31 and 35 would be opened and closed at the same time to establish or prevent circulation of a liquid through the hydraulic leg of which the valves are a part. Check valve 9 prevents liquid in tubing 8 from flowing through an open valve 35 and into reservoir 32 through its outlet tubing.

A remotely actuated valve 40 receiving circulating liquid from tubing 30 controls whether that liquid may enter the rightmost parallel leg of the hydraulic circuit as shown in FIG. 1. When valve 40 is open, the flowing liquid is transmitted to a reservoir 41. Reservoir 41 provides reserve volume for the addition of liquids from other external reservoirs into the flowing liquid. In order to avoid increasing the pressure within the hydraulic circuit, a specialized check valve 42 is hydraulically connected to the input tubing of reservoir 41. Check valve 42 allows excess gas, such as air, to escape from the hydraulic circuit, but prevents the flow of liquid out of the hydraulic loop. If liquid could flow out, concentrations within the flowing liquid could change and introduce errors into the titration process described below. The output tubing from reservoir 41 is connected to check valve 10 that prevents circulating liquid in tubing 8 from entering the output tubing of reservoir 41.

In the titration process described in more detail below, indicator solutions and titrant normally added to the hydraulic circuit during controlled cycles. A reservoir 45 contains indicator liquid. Liquid may be drawn from reservoir 45 when a remotely actuated valve 46 is open so that the liquid may flow into a pump 47. When valve 46 is opened and pump 47 is actuated, the indicator fluid is pumped through a check valve 48 into the input tubing to reservoir 41. Check valve 48 prevents the flow of circulating fluid from the hydraulic circuit from entering the output port of pump 47.

A liquid titrant is contained within a reservoir 49 may be admitted to pump 47 through a remotely actuated valve 50. Again, pump 47 extracts and pumps a known quantity of titrant through check valve 48 and into reservoir 41.

Pump 47 can be any of the known pumps in which the volume of liquid pumped is readily controlled and determined. One such pump pumps a known volume of liquid in one cycle of a piston within a cylinder. When the piston is withdrawn, a known volume of liquid is drawn into the cylinder. When the piston is driven into the cylinder, the known volume of fluid is driven out of the pump. Typically, these pumps respond to an electrical pulse or cycle by taking in and then expelling a known volume of a liquid. By applying a known number of electrical pulses to these pumps, a known number of known-volume increments of a liquid can be abstracted from a source, such as reservoirs 45 and 49, and injected into a portion of another hydraulic circuit such as reservoir 41. Pump 47 may also be a peristaltic pump. Peristaltic pumps employ flexible tubing and a motor driven roller that bears on and collapses the tubing to drive a liquid of known volume through the tube. Each revolution of the roller or pair of rollers corresponds to the pumping of a known volume of a liquid. By counting the motor and/or roller revolutions or by timing the "on" time of a pump motor having a fixed number of revolutions per minute, the quantity of liquid pumped can be easily determined. The pump motor may also be a stepper motor that responds to each applied pulse with fixed angular change in shaft position. By counting the pulses applied to a stepper motor in a peristaltic pump, the volume of liquid pumped can be calculated. Counting of pulses or measurement of total pumping time (by measuring the duration of an actuating signals) is performed by computer 5.

Controlled quantity pumps are commercially available from a number of sources, such as scientific supply houses including Fisher Scientific Company of Pittsburgh, Penn. FIG. 1 indicates a single pumping block 47 for use with both of reservoirs 45 and 49. Separate volume controlled pumps may be employed with each of reservoirs 45 and 49 or a single pump can be used since in the preferred titrating process described below, only one of those liquids is injected into the hydraulic circuit at any given time. However, to prevent any contamination between indicator and titrant, it may be preferable to employ separate pumps for each of reservoirs 45 and 47. As indicated in FIG. 1, pumping means 47 is controlled by computer 5 which can control and count the number of electrical pulses or cycles applied to the pump or the duration of the pump's operation, in order to calculate the volume of liquid injected by the pump.

In addition to the hydraulic circuit just described, FIG. 1 includes additional elements for periodic cleansing of the hydraulic circuit. A source of a cleansing fluid, such as water, is indicated as a reservoir 60. In a cleansing cycle, cleansing fluid is drawn from reservoir 60 by opening a remotely actuated valve 61. A check valve 62 prevents the flow of any liquid that is present in the hydraulic system back into reservoir 60 where it might contaminate the cleansing fluid. Remotely actuated valve 7 is also opened. Cleansing fluid may be pumped through the hydraulic circuit by pump 20, preferably with valves 21, 23, 26, 27, 31, 35 and 40 open, and with valves 4, 34, 46 and 50 closed. After a sufficient amount of cleansing fluid has been admitted to the hydraulic circuit, valve 61 may be closed. Eventually, valve 34 to the drain is opened and the circulating cleansing fluid is permitted to flow out of the hydraulic circuit.

In a separate cleansing step, valves 21 and 23 are actuated so that no liquid may flow into valve 21 from tubing 8 and no liquid may flow out of valve 23 in the direction of cells 24 and 25. Rather, cleansing liquid admitted through valve 61, with valve 7 closed, is circulated by a pump 63 into valve 23 and through filter 22. That flow is in a direction reverse to that produced when pump 20 is actuated. The reverse flowing cleansing liquid flows into valve 21 and out to a drain or sump, not shown. This back flushing removes particulate matter trapped by filter 22. At the conclusion of the cleansing cycle, valves 21 and 23 are returned to their normal positions, as are valves 7 and 61, as necessary.

In order to understand the preferred titration process, reference is made to FIG. 2 in which a test cell construction 101, such as might be employed as cells 24 and 25 of FIG. 1, is shown in a sectional view. Cell 101 includes a body 102 that may be molded or machined from a synthetic material such as a plastic or from metal. Preferably body 102 is machined aluminum. Body 102 includes opposed inlet and outlet ports through which light-transmissive tubing 103 passes. Tubing 103 may be glass or a flexible or rigid plastic. O-rings 104 and 105 are disposed between tubing 103 and body 102 proximate the inlet and outlet ports. The O-rings form light seals and frictionally retain body 102 in place along tubing 103. Cell 101 contains, within body 102 and tubing 103, a cavity 107 for containing a liquid. Cavity 107 is contained entirely within the walls of tubing 103 so that the liquid never contacts body 102.

Two opposed openings 110 and 111 are formed in body 102. Those openings are generally coaxial, disposed opposite each other and their common axis is preferably transverse to the direction of liquid flow through cavity 107. A light source, such as a light emitting diode, 112 is positioned within cavity 110 so that light emanating from the source is transmitted into cavity 107. Leads 113 extending from source 112 are connected in electrical circuitry as explained below in connection with FIG. 3.

A photosensor 120 is disposed within opening 111. Photosensor 120 may be a photocell, i.e. a resistor that varies in response to the quantity of incident light, or may be a photovoltaic cell, i.e. a photosensor that generates a voltage in response to incident light. Photosensor 120 includes electrical terminals 121 that are connected to electrical circuitry, such as the embodiment described below in connection with FIG. 3.

In the titration process described below, light transmitted from source 112 is detected by photosensor 120. The quantity of light received by photosensor 120 provides an indication of the color density of the fluid within cavity 107 and, thereby, provides the information from which to determine the chemical characteristic of the liquid disposed within the cavity. In order to avoid errors, extraneous light is excluded from cell 101 by constructing the cell from an opaque material, by coating its external surfaces with an opaque material or by enclosing the cell within an opaque housing. In either case, it is preferred that cells 24 and 25 of FIG. 1 be of identical construction. Light source 112 and photosensor 120 may be retained in position in their respective cells by an adhesive, such as silicon rubber or other removable adhesive that permits replacement of these elements.

The interaction of the components of the apparatus in FIG. 1 and 2 can be best understood through an example of the titration process performed by the apparatus. The example assumes that the hydraulic circuitry of FIG. 1 is clean and that no liquid is present in the apparatus except in reservoirs 3, 45 and 49. The apparatus begins with a sampling cycle in which the liquid having a chemical characteristic that is to be determined in introduced into the apparatus. To initiate that step, valves 21, 23, 26, 27, 31 and 34 are opened. (Valves 21 and 23 are in their normally open position, not the alternative filter cleaning position.) All other valves are closed. To admit liquid from reservoir 3 into the hydraulic circuit, valve 4 is opened and pump 20 is actuated. The liquid having the chemical characteristic to be determined is drawn into the hydraulic circuit and pumped through cells 24 and 25 into reservoir 32. The liquid flows out of the circuit through valve 34. This step is carried out for a sufficient time to fill cells 24 and 25 and the related tubing. Reservoir 32 provides reserve volume since, generally, the rate of flow through valve 34 is less than that through valve 4. At the conclusion of the sampling step, valves 4 and 34 are closed, preferably in that sequence. At the same time, or shortly thereafter, valve 35 is opened so that a hydraulic circuit is maintained.

In the next cycle, an indicator liquid from reservoir 45 is added to the liquid being tested. The indicator liquid is a solution that optically responds to a particular ion species by changing its color. That is, the indicator causes the solution color to change and, therefore, produces a change in the amount of light that is transmitted through a particular thickness of the liquid. Preferably, the indicator has a sharp, very narrow optical response of the familiar sigmoidal type. That is, when the concentration of the species to which the indicator is sensitive exceeds a threshold, a very substantial change in the color of the liquid is produced. Indicators that are sensitive to particular changes in pH include methyl orange xylene cyanol, methyl red, litmus, bromophenol blue, phenolphthalein and alizarin yellow. Others indicators sensitive to different species not involving pH are known and can be easily used in invention. For example iron titrations can employ a potassium permanganate indicator and a sodium sulfite titrant. Nitrite titrations can employ potassium permanganate as both an indicator and a titrant. In carrying out the titration, it is important that the indicator be thoroughly mixed with the liquid being analyzed. It is preferable that the quantity of indicator added be known. In the apparatus of FIG. 1, the indicator is added after opening valve 40 and subsequently isolating the hydraulic leg containing valve 31. The isolation is accomplished by first closing valve 31 and then permitting reservoir 32 to be drained through valve 35. The drainage readily occurs since check valve 33 admits air into reservoir 32. After a time sufficient to drain reservoir 32, valve 35 is closed.

At the direction of computer 5 or other system controller, valve 46 is opened and pump 47 actuated to inject a known volume of indicator from reservoir 45 into the liquid being circulated through reservoir 41. Pump 20 continues to circulate the fluid around the hydraulic loop including cells 24 and 25 as well as reservoir 41. Excess air pressure resulting from the injection of the indicator is relieved through check valve 42 which permits air to pass out of the system, but prevents any of the liquid from exiting. When a sufficient quantity of indicator has been added, valve 46 is closed and pump 47 is turned off. After a further period during which pump 20 circulates the fluid to ensure good mixing, cell 24 is isolated by closing valves 25 and 26.

By isolating cell 24, a reference sample is established having a light transmissivity that will be employed to determine when sufficient titrant has been added to the liquid in cell 25 to produce the expected optical response of the indicator. Cell 24 and cell 25 are herein referred to as a reference cell and a measuring cell, respectively.

After the isolation of cell 24, valve 50 is opened to supply a known-concentration titrant to pump 47 for injection into the liquid circulating through cell 25. The titrant introduction process is the same as the indicator introduction process described above, except for the liquid injected and the time sequence of injection, as explained below. The titrant may be an acid or base if the purpose of the titration is to determine the alkalinity or acidity of the liquid abstracted from vessel 3. The choice of the acid or base is generally not critical and the cheapest available common reagent, such as sulfuric acid, hydrochloric acid, sodium hydroxide or potassium hydroxide, may be used as a titrant. As mentioned above, when permanganate indicators are used, the titrant may be sodium sulfite or even potassium permanganate. In any event, the materials from which the valves and pumps employed in the apparatus are made must be chosen to withstand exposure to the titrants and indicators employed in a particular application.

Preferably, titrant is added in known volume increments by pump 47 at intervals separated in time. After a quantity of titrant is injected into the hydraulic circuit, pump 20 continues its circulation so that the titrant becomes mixed with the liquid in the circuit. After sufficient time for mixing, the amount of light transmitted through cells 24 and 25 is measured and compared. The amount of light transmitted is measured in the form of an electrical signal, as explained below in connection with FIG. 3. If the difference in the amounts of light transmitted (i.e. the difference between the electrical signals produced by the photosensors) is below a prescribed threshold valve, a system control, such as computer 5, concludes that the indicator has not yet changed color. In that event, computer 5 sends an additional signal so that pump 47 introduces an additional increment of titrant into the hydraulic circuit. After sufficient time for mixing, the amount of light transmitted through each of cells 24 and 25 is again compared. This iteration is continued until the prescribed, threshold value of difference between transmitted light values is met or exceeded. At that point, the titration is complete. The control means then calculates the quantity of titrant added in order to bring about the change in the optical characteristics of the indicator in the liquid. As noted above, the total quantity can be determined, in a preferred embodiment, by counting the number of electrical pulses applied to pump 47 and multiplying that number by the known volume pumped in response to each applied pulse. Employing conventional quantitative chemistry calculations, the chemical characteristic, such as a species concentration, can be determined.

At the completion of the titration process, the hydraulic circuit is cleansed in the cycle described above, to prepare it for a subsequent titration. Depending upon the results of the preceding titration, reagents may be added to the liquid in vessel 3 in order to bring the concentration of particular species within desired limits. The titration result may trigger automatic equipment that chooses the reagent and the quantity of that reagent that is to be added to vessel 3 to meet specifications. Alternatively, if after a maximum quantity of titrant has been added without detecting a change in the light transmitted through cell 25 relative to that transmitted through cell 24, computer 5 or other control means initiates an alarm indicating that the apparatus may have failed or that there is a serious error in the consitituents in vessel 3.

The apparatus can be used to establish a reference value for the threshold change indicating a completed titration. The reference value is established by carrying out the titration process using a liquid having the chemical characteristic of interest, but in a known concentration. Rather than introducing titrant in during numerous intervals, each separated in time from the next, a relatively large quantity of a known-concentration titrant is introduced into the liquid plus indicator present in the hydraulic circuit. The quantity of titrant introduced is chosen to be more than sufficient to produce the expected optical response of the indicator in the known liquid. The resulting change in the relative amounts of light transmitted through cells 24 and 25 is measured in terms of the electrical signal change measured, as explained below. The magnitude of this change can be multiplied by a factor less than one to establish the prescribed threshold value at which titration process employing a liquid having a quantitatively unknown species concentration is considered complete. Failure to observe the expected change indicates a probable malfunction in the apparatus.

Turning now to FIG. 3, a schematic illustration of electrical circuitry that may be employed in the invention is shown. Cells 24 and 25 are each fitted with a light source and a photosensor. Cell 24 includes a light source 150 that may be a light emitting diode. Cell 25 includes a similar, preferably identical, light source 151. Light sources 150 and 151 are connected electrically in parallel with a power source 153. Current limiting resistors 154 and 155 are connected in series with sources 150 and 151, respectively. While the source of light is shown to be independent for each of cells 24 and 25, a single light source may be used to transmit light through the cells. In that latter instance, mirrors, lights guides, such as fiber optic bundles, a beam splitter or the like may be used to direct the light from a single source to each of the cells. When a single light source is employed, there is no concern over variations of intensities of separate light sources.

A photosensor 160 is disposed in cell 24 opposite light source 150. A second photosensor 161 is disposed in cell 25 opposite light source 151. Photosensors 160 and 161 shown in FIG. 3 are photocells. That is, each is a resistor having a resistance value that varies in response to the quantity of light incident on the cell. Cells 160 and 161 are connected electrically in series and an electric current is supplied to them from a constant voltage source 162.

The negative sense terminal of a differential amplifier 163 is electrically connected to the electrical line that connects one terminal of photosensor 160 to a terminal of photosensor 161. The output terminal of amplifier 163 is also connected to the negative sense input terminal of the operational amplifier as a feedback loop. The positive sense input terminal of the amplifier is connected to ground. Since light sources 150 and 151 are similar or identical, essentially the same amount of light reaches each of sensors 160 and 161 when the same liquid is disposed in each of cells 24 and 25 between the respective sources and sensors. Likewise, photosensors 160 and 161 are chosen to have matched photoresponses. Differences in the intensity and spectral content of the light emitted by sources 150 and 151 and in the spectral and absolute responses of photosensors 160 and 161 may be compensated by modifying the circuit shown. A potentiometer may be inserted in the series electrical connection between photosensors 160 and 161. The wiping contact of the potentiometer is connected to the negative sense input terminal of amplifier 163. With empty cells 24 and 25 or with the same liquid disposed in the cells, the absolute value of the output signal from amplifier 163 is brought to a minimum by adjusting the potentiometer. This "zero setting" step compensates for both light source and photosensor characteristic variations.

When each of sensors 160 and 161 has essentially the same resistance, or are balanced with a variable resistor to have essentially the same resistance, the voltage produced by constant voltage source 162 is evenly divided between the sensors. When a reference mixture of a liquid and indicator is isolated in cell 24, the amount of light reaching sensor 160 is stable. However, as titrant is added to the liquid flowing through cell 25 and interposed between light source 151 and 161, the light received by sensor 161 may change. The titrant may cause an indicator to lighten in intensity resulting in an increased amount of light reaching sensor 161, or it may result in a darker mixture reducing the amount of light reaching sensor 161. In either case, when the light reaching sensor 161 changes, the voltage produced by constant voltage source 162 is unequally divided between sensors 160 and 161. This imbalance, when large enough, results in a significant change in the magnitude of the output signal from differential amplifier 163. That is, the amplifier outputs a signal which constitutes a comparison of the voltage drop across one photosensor with the voltage drop across the other photosensor and produces a significant signal change when the comparison changes significantly. When an indicator having a sigmoidal response curve is employed, the variation from the balance is small until the critical portion of the response curve is reached. Beyond that point a large change in the output signal from amplifier 163 is observed. The direction of change of that signal depends upon whether the indicator changes from light to dark or dark to light in response to the addition of titrant. The magnitude of the change has been observed to be quite large, as much as 40%, so that the completion of the titration process is well defined.

Other electrical circuitry can be used to process the compared signals. Logic gates and/or comparators may be substituted for amplifier 163. Amplifier 163 may be removed altogether and the balance signal from the connection of photosensors 160 and 161 may be supplied directly to computer 5. In that case, the signal may be digitized before the threshold difference comparison test is applied. Thus the comparison would employ a digital signal rather than the analog signals compared in amplifier 163.

Preferably computer 5 initiates, on command or at fixed time intervals, a titration and cleansing sequence. The results of the titration may generate messages on the computer terminal, actuate apparatus to take steps to correct a detected deficiency in the tested liquid, create automated records and/or actuate alarms. The process control thus achieved is simple and relatively low in cost.

A particular advantage of the apparatus and method described lies in the use of a reference cell 24. Regardless of the initial intensity of the liquid being monitored and analyzed, the apparatus can perform the desired titration. This advantage is achieved because the titration does not depend on the initial or final color of the liquid being monitored or analyzed, but rather depends upon a change in the intensity in a titrated sample relative to the intensity of a reference sample. This advantage overcomes the difficulties associated with known colorimetry techniques that have been successfully applied in manufacturing only at relatively high costs.

The invention has been described with reference to certain preferred embodiments. Various modifications and additions within the spirit of the invention will occur to those of skill in the art. Accordingly, the scope of the invention is limited solely by the following claims.

I claim:

1. A method for determining a chemical characteristic of a liquid comprising:
    disposing the liquid having a chemical characteristic in both reference and measuring test cells, said cells being at least partially transparent to light;
    adding an indicator to said liquid so that the liquid disposed in at least said measuring test cell contains the indicator, said indicator responding to a titrant to alter the optical transmission of the liquid containing the indicator;
    transmitting light through said reference and measuring cells;
    generating first and second electrical signals respectively indicative of the amount of light transmitted through said reference and measuring cells;
    comparing said first and second signals to each other;
    adding a titrant to said measuring cell, said titrant responding to said chemical characteristic by altering the optical transmission of said liquid containing said indicator, and repeating said comparing and adding titrant steps until the difference between said first and second signals satisfies a prescribed condition; and
    determining the volume of titrant added to said liquid to satisfy said prescribed condition, whereby said chemical characteristic can be determined.

2. The method of claim 1 wherein said indicator is chosen from the group consisting of methyl orange xylene cyanol, methyl red, litmus, bromophenol blue, phenolphthalein, and potassium permanganate.

3. The method of claim 1 wherein said titrant is chosen from the group consisting of an acidic solution, a basic solution, sodium sulfite, and potassium permanganate.

4. The method of claim 1 including adding titrant to said measuring cell in known volume increments and determining the volume of titrant added by counting the number of increments added.

5. The method of claim 1 including quantitatively determining the chemical characteristic of the liquid from the volume of titrant added to said measuring cell to reach or exceed said prescribed value.

6. The method of claim 1 including flowing a cleansing liquid through said reference and measuring cells before disposing said liquid having a chemical characteristic in said cells.

7. The method of claim 1 including establishing a reference for said prescribed value by disposing a liquid having a quantitatively known chemical characteristic in said reference and measuring cells, adding said indicator to said liquid and adding said titrant to said measuring cell in a quantity sufficient to produce a color change in the liquid and indicator mixture in said measuring cell, measuring the difference between said first and second signals after said color change and multiplying said difference by a factor less than one to obtain said prescribed value.

8. The method of claim 1 wherein indicator is added so that liquid disposed in both said reference and measuring test cells contains the indicator.

9. The method of claim 1 wherein said prescribed condition is satisfied by the difference between said first and second signals reaching or exceeding a prescribed value.

10. An apparatus for determining a chemical characteristic of a liquid comprising:
    at least one light source;
    reference and measuring cells, each cell for receiving and containing a liquid and being transparent to at least some of the light produced by said at least one light source;
    means for disposing the liquid in both said cells;
    a first reservoir for containing a liquid indicator and first means for controllably introducing indicator into the liquid disposed in at least said measuring cell;
    a second reservoir for containing a liquid titrant and second means for controllably introducing titrant from said second reservoir into the liquid disposed in said measuring cell;
    first and second photosensors for receiving light transmitted from said at least one source through said reference and measuring cells, respectively, and for generating first and second electrical signals, respectively, indicative of the amount of light transmitted through said reference and measuring cells;
    comparing means for comparing said first and second electrical signals to each other; and
    control means for controlling operation of said second means for introducing in response to the comparison of said first and second signals.

11. The apparatus of claim 10 including pumping means for pumping a liquid and a hydraulic circuit wherein said reference and measuring cells are hydraulically connected to each other in parallel, said parallel cells are hydraulically connected in series with said pumping means, and said first and second introducing means are connected to introduce indicator and titrant, respectively, into said circuit.

12. The apparatus of claim 10 wherein said second means for introducing comprises an electrically driven pump for pumping a known volume of titrant in response to the application of an electrical pulse to said pump and counting means for counting the number of pulses applied to said pump.

13. The apparatus of claim 12 including means for actuating said second means for introducing until the difference between said first and second signals satisfies a prescribed condition.

14. The apparatus of claim 10 wherein said second means for introducing comprises an electrically driven pump for pumping titrant at a known rate and timing means for measuring the time said pump is actuated.

15. The apparatus of claim 10 wherein said reference and measuring cells have substantially identical optical characteristics.

16. The apparatus of claim 10 including filtering means for filtering particulate matter from liquid flowing into said reference and measuring cells.

17. The apparatus of claim 10 including pumping means for circulating liquids through selected ones of said reference and measuring cells.

18. The apparatus of claim 10 including means for isolating said reference cell to prevent introduction of said titrant into said reference cell.

19. The apparatus of claim 10 including a third reservoir in communication with said measuring cell for accommodating the increased volume produced by introduction of titrant into the liquid.

20. The apparatus of claim 10 including means for introducing a cleansing liquid into said reference and measuring cells.

21. The apparatus of claim 20 including pumping means for circulating the cleansing liquid through said reference and measuring cells.

22. The apparatus of claim 10 wherein said comparing means comprises a computer.

23. The apparatus of claim 10 wherein said control means comprises a computer.

24. The apparatus of claim 10 including means for actuating said second means for introducing until the difference between said first and second signals reaches or exceeds a prescribed value.

* * * * *